United States Patent [19]
Prosise et al.

[11] Patent Number: 6,117,416
[45] Date of Patent: *Sep. 12, 2000

[54] MOUTHWASH COMPOSITION INCLUDING A SOLVENT-FREE HIGH MOLECULAR WEIGHT UNCROSSLINKED TERPOLYMER OF MALEIC ANHYDRIDE $C_1$-$C_4$ ALKYL VINYL ETHER AND ISOBUTYLENE

[75] Inventors: William E. Prosise, Ramsey; James F. Curry, Wayne; Krystyna Plochocka, Scotch Plains, all of N.J.

[73] Assignee: ISP Investments Inc., Wilmington, Del.

[ * ] Notice: This patent is subject to a terminal disclaimer.

[21] Appl. No.: 09/396,026

[22] Filed: Sep. 15, 1999

Related U.S. Application Data

[63] Continuation-in-part of application No. 08/942,830, Oct. 2, 1997, Pat. No. 5,939,506, and a continuation-in-part of application No. 09/097,895, Jun. 16, 1998, Pat. No. 6,046,291.

[51] Int. Cl.[7] ............................. A61K 7/16; C08F 222/06
[52] U.S. Cl. ........................... 424/49; 526/272; 526/332; 526/348.7
[58] Field of Search .................................. 526/272, 332, 526/348.1; 424/49

[56] References Cited

U.S. PATENT DOCUMENTS 5,082,913   1/1992   Tazi ........................................ 526/272

*Primary Examiner*—Fred Zitomer
*Attorney, Agent, or Firm*—Walter Katz; William J. Davis; Marilyn J. Maue

[57] ABSTRACT

This invention relates to a mouthwash composition including a solvent-free, high molecular weight (>1,500,000) uncrosslinked terpolymer of maleic anhydride, a $C_1$–$C_4$ alkyl vinyl ether and isobutylene.

6 Claims, No Drawings

MOUTHWASH COMPOSITION INCLUDING A SOLVENT-FREE HIGH MOLECULAR WEIGHT UNCROSSLINKED TERPOLYMER OF MALEIC ANHYDRIDE $C_1$-$C_4$ ALKYL VINYL ETHER AND ISOBUTYLENE

CROSS-REFERENCE TO RELATED U.S. PATENT APPLICATION

This application is a continuation-in-part of U.S. patent application Ser. No. 08/942,830, filed Oct. 2, 1997, U.S. Pat. No. 5,939,506, and Ser. No. 09/097,895, filed Jun. 16, 1998, U.S. Pat. No. 6,046,291, both assigned to the same assignee as herein.

BACKGROUND OF THE INVENTION

1. Field of the Invention

This invention relates to a mouthwash composition, and, more particularly, to a formulation including a solvent-free, high molecular weight (>1,500,000) uncrosslinked terpolymer of maleic anhydride (MAN), a $C_1$-$C_4$ alkyl vinyl ether (AVE), and isobutylene (IB).

2. Detailed Description of the Prior Art

U.S. Pat. No. 5,037,924 described the preparation of terpolymers of maleic anhydride, a $C_1$-$C_4$ alkyl vinyl ether, and isobutylene, for use as denture adhesives in the form of their mixed salts. These terpolymers were made by precipitation polymerization in the presence of an added solvent, for example, a cosolvent system of ethyl acetate and cyclohexane. The resultant terpolymer had a low molecular weight of about 30,000 to 400,000, with relatively good performance, in the form of their mixed salts, as denture adhesives. Furthermore, the terpolymers and their salts made therein in U.S. Pat. No. 5,037,924 contain trace amounts of the ethyl acetate and cyclohexane solvents.

U.S. Pat. No. 5,334,375 described dentifrice composition containing crosslinked copolymers of MAN, an AVE and IB, for controlling plaque.

Accordingly, it is an object of this invention to provide a mouthwash composition including solvent-free, uncrosslinked terpolymers of MAN, an AVE and IB, with molecular weights of at least 1,500,000, which will perform in an improved and effective manner for retention of the antibacterial agent therein on teeth.

These and other objects and features of the invention will be made apparent from the following more particular description of the invention.

SUMMARY AND DETAILED DESCRIPTION OF THE INVENTION

What is described herein is a mouthwash composition including a solvent-free, high molecular weight (>1,500,000) uncrosslinked terpolymer of maleic anhydride (MAN), a $C_1$-$C_4$ alkyl vinyl ether (AVE) and isobutylene (IB), having molecular structure of $(A-B)_n$, where A=MAN and B=AVE or IB and containing preferably about 5 to 45 mole % of isobutylene.

The NMR spectra of these terpolymers show an alternating molecular structure $(A-B)_n$ as described above, where n is such that the terpolymer has a weight average molecular weight (GPC, water pH 9) in excess of about 1,500,000, and a specific viscosity which is $\geq 6$ (1% in DMF, 25° C.).

The terpolymers used in the mouthwash composition of the invention is made by a solvent-free process which is carried out by charging the alkyl vinyl ether and isobutylene into a reactor at a mole ratio of isobutylene to alkyl vinyl ether which is substantially greater than that desired in the terpolymer, adding a radical initiator, heating the mixture to a reaction temperature of about 50° to 100° C., and feeding molten maleic anhydride over time into the reactor, wherein the mole ratio of maleic anhydride to the total charge of alkyl vinyl ether and isobutylene is not higher than 1:3. The resulting terpolymers are odorless and free of the trace amounts of solvents characteristic of other known processes for making such terpolymers.

The terpolymers have a compositional ratio of maleic anhydride to alkyl vinyl ether to isobutylene of about 0.50:0.45–0.05:0.05–0.45, respectively. Preferably the terpolymer includes about 5–25 mole % of IB based on the total amount of alkyl vinyl ether and IB therein. The molecular weight is at least 1,500,000 (GPC, water, pH 9), and the specific viscosity (SV) is $\geq 6$ (1% in DMF, 25° C.).

The terpolymers are obtained as solvent-free, fine white powders.

A feature of the process of the invention is a solvent-free polymerization process which is carried out using an excess of alkyl vinyl ether and isobutylene as the reaction medium. Accordingly, the polymerization reaction is carried out by precharging an AVE/IB mixture of predetermined composition into the reactor, adding a radical initiator, heating to a reaction temperature of about 50° to 100° C., and feeding molten maleic anhydride into the reactor over time.

The mole ratio of MAN to the total of MVE+IB is not higher than 1:3, preferably less than 1:5. Furthermore, the mole ratio of IB to MVE in precharge is made significantly higher than that desired in the terpolymer, preferably about 1:1 IB:MVE for a terpolymer containing 1:2 IB:MVE and about 1:2 IB:MVE for a terpolymer containing 1:4 IB:MVE.

Generally, an additional amount of MVE is added near the end of the polymerization in order to complete use of MAN reactant.

After stripping the remaining MVE and IB, the product is obtained as a fine odorless powder, without a solvent.

The invention will now be described with reference to the following examples.

EXAMPLE 1

A 1-liter Parr stainless steel reactor equipped with an agitator, heating mantle and syringe pumps for charging reagents was sparged with nitrogen and charged with 175 g (3.00 mole) of methyl vinyl ether (MVE), 175 g (3.12 mole) of isobutylene (IB) and 0.10 g of lauroyl peroxide. The mole ratio of MVE to IB was 0.96. The charged reactor was heated to 63° C. and the temperature was maintained while molten maleic anhydride (MAN) in an amount of 39.2 g (0.400 mole) was fed into the reactor over a period of 2 hours. The mole ratio of MVE and IB to MAN was 15.3. After holding for 3 hours at 65° C., an additional amount of 50 g (0.86 mole) MVE was added. Then the temperature was raised to 70° C. and maintained for 1 hour. Thereafter the reactor was cooled to room temperature, the pressure was released and the reactor discharged. The reaction product was recovered as a fine, white powder which was dried for 1 hour in a vacuum oven at 65° C. The product was a uniform, fine white powder (62 g), without any unreacted MAN. The specific viscosity (SV), as measured in a 1% DMF solution at 25° C. was 6.94. A $^{13}$C NMR spectrum showed that the mole ratio of monomers in the terpolymer of MAN:MVE:IB was 0.50:0.34:0.16. The weight average molecular weight (GPC, water, pH 9) of the powder was at least 1,500,000.

EXAMPLES 2–5

The procedure of Example 1 was followed to provide terpolymers having different ratios of MAN:MVE:IB. The results are shown in Table 1 below.

TABLE 1

| | Example No. | | | |
|---|---|---|---|---|
| Polymer | 2 | 3 | 4 | 5 |
| MVE, g (mol) | 100 (1.72) | 200 (344) | 167 (2.87) | 200 (3.44) |
| IB, g (mol) | 150 (2.67) | 50 (0.89) | 83 (1.49) | 25 (0.44) |
| MAN, g (mol) | 41 (0.418) | 41 (0.418) | 41 (0.418) | 41 (0.418) |
| MVE/IB ratio in the reaction (by mole) | 0.39:0.61 | 0.79:0.11 | 0.66:0.34 | 0.89:0.11 |
| MAN:MVE:IB ratio in polymer (by $^{13}$C NMR, in mole fractions) | 0.50:0.28:0.21 | 0.50:0.46:0.07 | 0.50:0.40:0.10 | 0.50:0.44:0.05 |
| SV (1%, DMF) | 7.71 | 11.11 | 6.96 | 14.46 |
| Mw (GPC, water, pH 9) | >1,500,000 | >1,500,000 | >1,500,000 | >1,500,000 |

Test Method

An in vitro test was used to evaluate the performance of a given polymer in a mouthwash formulation including an essential oil which functions as an antibacterial/antiseptic as well as a flavoring agent. Generally, the polymer is included in an amount of about 0.1 to 5% by weight of the composition, preferably about 0.2–1%. The test measured the essential oil* *e.g. thymol, which is an antibacterial/antiseptic commonly used in mouthwash formulation retention and uptake after the polymer was applied to the surface of hydroxy apatite (HAP), an artificial tooth surface. This test is correlative with actual use of a mouthwash formulation followed by rinsing with water.

HAP is a mineral phase of teeth which can provide a uniform surface size, and allow for quantitative and reproducible results. The HAP material was prepared in the form of a disc as per reference by placing in a die having a diameter of 13 mm and compressing. Then the resultant pellet was dried and finally sintered at 800° C. for 4 hours.

Uptake of essential oil was measured by incubating the HAP disc in artificial saliva overnight at 37° C. and immersing it in a sample mouthwash solution containing a given polymer at 37° C. for 30 minutes with continuous shaking. The disc then was rinsed in distilled water and dried in a stream of air. The thus-treated disc was placed in acetonitrile solvent to extract the essential oil from the disc. The amount of essential oil present in the solvent was then determined by HPLC.

Retention of essential oil on the saliva-coated HAP disc was measured by treating the disc with the mouthwash solution, rinsing the disc with water, and reincubating in artificial saliva for 60 minutes with continuous shaking. The disc was then removed from the saliva, rinsed with water and placed in acetonitrile. The amount of essential oil retained on the disc was measured by HPLC. The control sample did not contain any polymer.

The results are shown in Table 2 below

TABLE 2

| Ingredient | Control | Invention |
|---|---|---|
| Terpolymer of Invention (Ex. 2) | — | 0.60 g |
| Ethanol | 16.40 g | 16.40 |

TABLE 2-continued

| Ingredient | Control | Invention |
|---|---|---|
| Sorbitol (70%) | 25.72 | 25.72 |
| Thymol* | 0.06 | 0.06 |
| Eucalyptol* | 0.09 | 0.09 |
| Methyl Salicylate* | 0.06 | 0.06 |
| Menthol* | 0.04 | 0.04 |
| Poloxamer 407 | 0.50 | 0.50 |
| Water | 57.13 | 56.53 |

*essential oils (antiseptic/antibacterial/flavoring agent)

The invention mouthwash formulation had over a 50% increase over the control mouthwash uptake and retention of essential oils onto the artificial teeth.

Similar effective results were obtained using the terpolymers of Examples 1, 3, 4 and 5 in place of the terpolymer of Example 2.

The results herein demonstrate the effectiveness of including the new polymer in mouthwash compositions.

While the invention has been described with particular reference to certain embodiments thereof, it will be understood that changes and modifications may be made which are within the skill of the art. Accordingly, it is intended to be bound only by the following claims, in which:

What is claimed is:

1. A mouthwash composition including an antibacterial enhancing amount of a solvent-free, high molecular weight uncrosslinked terpolymer of maleic anhydride, a $C_1$–$C_4$ alkyl vinyl ether and about 5 to 45 mole % of isobutylene, which has a weight average molecular weight (GPC, water, pH 9) of at least 1,500,000, and a specific viscosity which is ≧6 (1% in DMF).

2. A mouthwash composition according to claim 1 in which the uncrosslinked terpolymer is made by charging the alkyl vinyl ether and isobutylene into a reactor, the mole ratio of isobutylene to alkyl vinyl ether being substantially greater than that desired in the terpolymer, adding a radical initiator, heating the mixture to a reaction temperature of about 50° to 100° C., feeding molten maleic anhydride into the thus charged reactor over time, the mole ratio of maleic anhydride fed therein to the total charge of alkyl vinyl ether and isobutylene being no higher than 1:3.

3. A mouthwash composition according to claim 1 wherein said $C_1$–$C_4$ alkyl vinyl ether is methyl vinyl ether.

4. A mouthwash composition according to claim 1 wherein the mole ratio of maleic anhydride to alkyl vinyl ether to isobutylene in the terpolymer is 0:50:0.45–0.05:0.05–0.45, respectively.

5. A mouthwash composition according to claim 1 which contains an essential oil which functions as an antibacterial/antiseptic and flavoring agent.

6. A mouthwash composition according to claim 1 in which said essential oil is thymol.

* * * * *